United States Patent
Carlsen et al.

(10) Patent No.: US 6,588,427 B1
(45) Date of Patent: Jul. 8, 2003

(54) HEAT AND MOISTURE EXCHANGER ADAPTER TO CLOSED SUCTION CATHETER ASSEMBLY AND SYSTEM HAVING IMPROVED CATHETER CLEANING

(75) Inventors: Wayne D. Carlsen, West Jordan, UT (US); Chet M. Crump, Draper, UT (US); Edward B. Madsen, Riverton, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/082,786

(22) Filed: Feb. 25, 2002

(51) Int. Cl.$^7$ .............................. A61M 16/00; A62B 9/06
(52) U.S. Cl. ........................... 128/207.14; 128/205.12; 128/205.19; 128/207.14; 604/35; 604/118; 604/264; 604/538; 604/539
(58) Field of Search ................. 128/207.16, 205.19, 128/207.14, 207.17, 205.12, 912; 604/533, 534, 535, 536, 538, 539, 35, 118, 264, 902

(56) References Cited

U.S. PATENT DOCUMENTS

| | | | |
|---|---|---|---|
| 3,556,097 A | | 1/1971 | Wallace |
| 3,782,083 A | | 1/1974 | Rosenberg |
| 3,815,754 A | | 6/1974 | Rosenberg |
| 3,825,001 A | * | 7/1974 | Bennett et al. ........ 604/170.02 |
| 3,831,629 A | | 8/1974 | Mackal et al. |
| 3,834,388 A | | 9/1974 | Saucer |

(List continued on next page.)

FOREIGN PATENT DOCUMENTS

| | | |
|---|---|---|
| EP | 0265163 A2 | 4/1988 |
| EP | 0730878 A2 | 9/1996 |
| WO | WO9721386 | 6/1997 |
| WO | WO9903526 | 1/1999 |
| WO | WO9960954 | 12/1999 |
| WO | WO0002610 | 1/2000 |
| WO | WO0145779 A1 | 6/2001 |
| WO | WO0172365 A1 | 10/2001 |

OTHER PUBLICATIONS

English language Abstract of EP 0 730 878 A2.
U.S. patent application No. 09/459,522, filed Dec. 13, 1999 (BAL–64).
U.S. patent application No. 09/471,317, filed Dec. 23, 1999 (BAL–55).
U.S. patent application No. 09/693,261, filed Oct. 20, 2000 (BAL–66–CIP–CON).
U.S. patent application No. 09/702,376, filed Oct. 31, 2000 (BAL–53).
U.S. patent application No. 09/702,375, filed Oct. 31, 2000 (BAL–54).
U.S. patent application No. 09/716, 486, filed Nov. 20, 2000 (BAL–66–CON).
U.S. patent application No. 09/741,769, filed Dec. 19, 2000 (KCX–384).

Primary Examiner—Weilun Lo
Assistant Examiner—Michael Mendoza
(74) Attorney, Agent, or Firm—Dority & Manning, P.A.

(57) ABSTRACT

An endotracheal suction catheter apparatus is provided. The apparatus includes a distal end that is configured for allowing a catheter to be moved through the distal end and into the respiratory tract of a patient. The distal end defines a cleaning chamber where the catheter may be cleaned. A flap is located in the distal end and is located on one end of the cleaning chamber. The flap effects fluid flow within the cleaning chamber during cleaning of the catheter. A connection member is present and is attached to the distal end. The connection member is configured for releasably engaging a heat and moisture exchanger so that the catheter may be advanced through the distal end into the heat and moisture exchanger.

25 Claims, 14 Drawing Sheets

U.S. PATENT DOCUMENTS

| | | |
|---|---|---|
| 3,881,482 A | 5/1975 | Lindholm |
| 3,902,500 A | 9/1975 | Dryden |
| 3,932,153 A | 1/1976 | Byrns |
| 3,937,220 A | 2/1976 | Coyne |
| 3,991,762 A * | 11/1976 | Radford ............ 604/119 |
| 4,009,720 A | 3/1977 | Crandall |
| 4,015,336 A | 4/1977 | Johnson |
| 4,036,616 A | 7/1977 | Byrns |
| 4,047,527 A | 9/1977 | Kelsen |
| 4,062,363 A * | 12/1977 | Bonner, Jr. ............ 604/171 |
| 4,090,513 A | 5/1978 | Togawa |
| 4,159,954 A | 7/1979 | Gangemi |
| 4,193,406 A | 3/1980 | Jinotti |
| 4,291,691 A | 9/1981 | Cabal et al. |
| 4,315,505 A | 2/1982 | Crandall et al. |
| 4,327,723 A * | 5/1982 | Frankhouser ............ 604/171 |
| 4,351,328 A | 9/1982 | Bodai |
| 4,405,163 A | 9/1983 | Voges et al. |
| 4,468,224 A | 8/1984 | Enzmann et al. |
| 4,508,533 A | 4/1985 | Abramson |
| 4,516,573 A | 5/1985 | Gedeon |
| 4,569,344 A | 2/1986 | Palmer |
| 4,573,965 A | 3/1986 | Russo |
| 4,573,979 A | 3/1986 | Blake |
| 4,574,173 A | 3/1986 | Bennett |
| 4,595,005 A | 6/1986 | Jinotti |
| 4,638,539 A | 1/1987 | Palmer |
| 4,646,733 A * | 3/1987 | Stroh et al. ............ 128/207.16 |
| 4,649,913 A | 3/1987 | Watson |
| 4,657,008 A | 4/1987 | Broddner et al. |
| 4,669,463 A * | 6/1987 | McConnell ............ 128/207.14 |
| 4,696,296 A * | 9/1987 | Palmer ............ 128/207.16 |
| 4,696,305 A | 9/1987 | von Berg |
| 4,705,073 A | 11/1987 | Beck |
| 4,798,676 A | 1/1989 | Matkovich |
| 4,805,611 A * | 2/1989 | Hodgkins ............ 128/207.14 |
| 4,825,859 A * | 5/1989 | Lambert ............ 128/202.16 |
| 4,834,726 A | 5/1989 | Lambert |
| 4,836,199 A * | 6/1989 | Palmer ............ 128/207.16 |
| 4,850,350 A * | 7/1989 | Jackson ............ 128/207.16 |
| 4,852,563 A | 8/1989 | Gross |
| 4,872,579 A * | 10/1989 | Palmer ............ 128/205.19 |
| 4,909,248 A | 3/1990 | McLennan Anderson |
| 4,929,426 A | 5/1990 | Bodai et al. |
| 4,938,741 A | 7/1990 | Lambert |
| 4,946,445 A | 8/1990 | Lynn |
| 4,967,743 A | 11/1990 | Lambert |
| 4,968,741 A * | 11/1990 | Burroway et al. ............ 524/710 |
| 4,969,878 A * | 11/1990 | Schmidt et al. ............ 604/264 |
| D312,880 S | 12/1990 | Bodai et al. |
| 5,029,580 A * | 7/1991 | Radford et al. ............ 128/207.14 |
| 5,042,468 A | 8/1991 | Lambert |
| D321,252 S | 10/1991 | Jepson et al. |
| 5,060,646 A | 10/1991 | Page |
| 5,067,496 A | 11/1991 | Eisele |
| 5,073,164 A | 12/1991 | Hollister et al. |
| 5,083,561 A | 1/1992 | Russo |
| 5,088,486 A | 2/1992 | Jinotti |
| 5,101,817 A * | 4/1992 | Etter ............ 128/200.26 |
| 5,104,389 A * | 4/1992 | Deem et al. ............ 604/264 |
| 5,107,829 A | 4/1992 | Lambert |
| 5,109,471 A | 4/1992 | Lang |
| 5,125,893 A | 6/1992 | Dryden |
| 5,134,996 A | 8/1992 | Bell |
| 5,139,018 A | 8/1992 | Brodsky et al. |
| 5,140,983 A | 8/1992 | Jinotti |
| 5,158,569 A | 10/1992 | Strickland et al. |
| 5,184,611 A | 2/1993 | Turnbull |
| 5,191,881 A | 3/1993 | Beck |
| 5,195,527 A | 3/1993 | Hicks |
| 5,201,309 A | 4/1993 | Friberg et al. |
| 5,201,717 A | 4/1993 | Wyatt et al. |
| 5,213,096 A | 5/1993 | Kihlberg et al. |
| 5,215,522 A | 6/1993 | Page et al. |
| 5,230,332 A | 7/1993 | Strickland |
| 5,242,084 A | 9/1993 | Jinotti |
| 5,254,098 A | 10/1993 | Ulrich et al. |
| 5,255,676 A | 10/1993 | Russo |
| 5,277,177 A | 1/1994 | Page et al. |
| 5,300,043 A | 4/1994 | Devlin et al. |
| 5,309,902 A | 5/1994 | Kee et al. |
| 5,309,904 A | 5/1994 | Beck |
| 5,325,850 A | 7/1994 | Ulrich et al. |
| 5,325,851 A | 7/1994 | Reynolds et al. |
| 5,333,606 A | 8/1994 | Schneider et al. |
| 5,333,607 A | 8/1994 | Kee et al. |
| 5,337,780 A | 8/1994 | Kee |
| 5,343,857 A | 9/1994 | Schneider et al. |
| 5,346,478 A | 9/1994 | Jinotti |
| 5,349,950 A | 9/1994 | Ulrich et al. |
| 5,354,267 A | 10/1994 | Niermann et al. |
| 5,355,876 A | 10/1994 | Brodsky et al. |
| 5,357,946 A | 10/1994 | Kee et al. |
| 5,368,017 A | 11/1994 | Sorenson et al. |
| 5,370,610 A | 12/1994 | Reynolds |
| 5,383,447 A | 1/1995 | Lang |
| 5,390,668 A | 2/1995 | Lehman |
| 5,390,669 A | 2/1995 | Stuart et al. |
| 5,435,298 A | 7/1995 | Anthony |
| 5,445,141 A | 8/1995 | Kee et al. |
| 5,449,348 A | 9/1995 | Dryden |
| 5,460,172 A | 10/1995 | Eckerbom et al. |
| 5,460,176 A | 10/1995 | Frigger |
| 5,460,613 A | 10/1995 | Ulrich et al. |
| 5,487,381 A | 1/1996 | Jinotti |
| 5,490,503 A | 2/1996 | Hollister |
| 5,496,287 A | 3/1996 | Jinotti |
| 5,513,627 A | 5/1996 | Flam |
| 5,513,628 A | 5/1996 | Coles et al. |
| D373,637 S | 9/1996 | Spearman |
| 5,578,006 A | 11/1996 | Schön |
| 5,582,161 A | 12/1996 | Kee |
| 5,582,165 A | 12/1996 | Bryan et al. |
| 5,590,644 A | 1/1997 | Rosenkoetter |
| 5,598,840 A | 2/1997 | Iund et al. |
| 5,605,149 A | 2/1997 | Warters |
| 5,628,306 A | 5/1997 | Kee |
| 5,642,726 A | 7/1997 | Owens et al. |
| 5,664,564 A | 9/1997 | Palmer |
| 5,664,594 A | 9/1997 | Kee |
| 5,676,136 A | 10/1997 | Russo |
| 5,687,714 A | 11/1997 | Kolobow et al. |
| 5,701,891 A | 12/1997 | Groenke |
| 5,715,815 A | 2/1998 | Lorenzen et al. |
| D393,722 S | 4/1998 | Fangrow, Jr. et al. |
| 5,735,271 A | 4/1998 | Lorenzen et al. |
| 5,769,702 A | 6/1998 | Hanson |
| 5,813,402 A | 9/1998 | Jinotti |
| 5,855,562 A | 1/1999 | Moore et al. |
| 5,882,348 A | 3/1999 | Winterton et al. |
| 5,906,201 A | 5/1999 | Nilson |
| 5,919,174 A | 7/1999 | Hanson |
| 5,992,413 A | 11/1999 | Martin, Jr. et al. |
| 6,033,455 A | 3/2000 | Kurashima |
| 6,095,135 A | 8/2000 | Clawson et al. |
| 6,105,576 A | 8/2000 | Clawson et al. |
| 6,131,573 A | 10/2000 | Brown |
| 6,227,200 B1 | 5/2001 | Crump et al. |
| 6,248,099 B1 | 6/2001 | Bell |
| 6,363,930 B1 | 4/2002 | Clawson et al. |
| 6,422,235 B1 * | 7/2002 | Persson ............ 128/200.26 |

\* cited by examiner

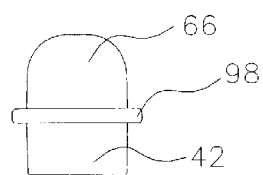
FIG. 12B
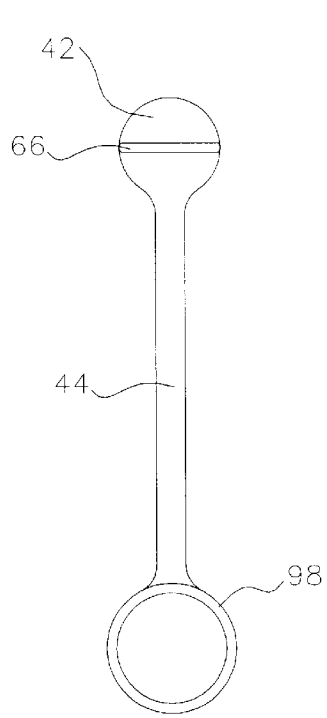 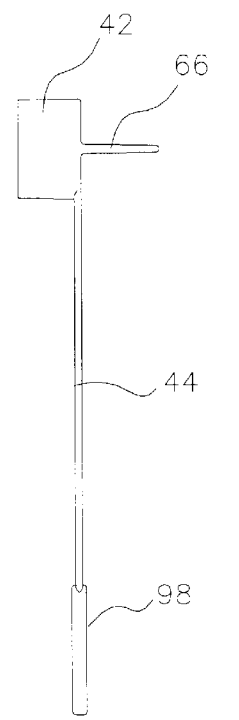 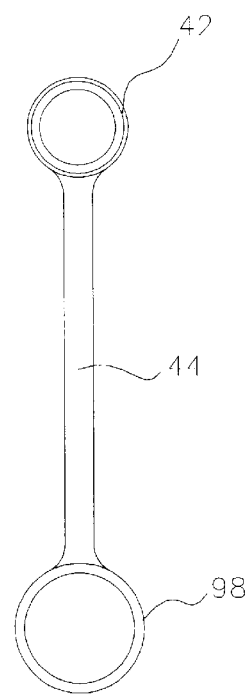
FIG. 12C    FIG. 12D    FIG. 12E
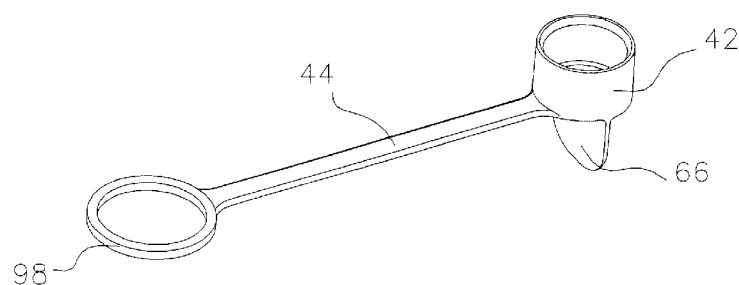
FIG. 12A

HEAT AND MOISTURE EXCHANGER ADAPTER TO CLOSED SUCTION CATHETER ASSEMBLY AND SYSTEM HAVING IMPROVED CATHETER CLEANING

BACKGROUND

There are a number of different circumstances in which it is necessary for a person to have an artificial airway, such as a tracheostomy tube, placed in his or her respiratory tract. As used herein, the phrase "artificial airway" includes devices such as tracheostomy tubes, endotracheal tubes and the like. Artificial airways keep the patient's natural airway open so that adequate lung ventilation can be maintained. In particular situations, the artificial airway must be left in the patient for a prolonged period of time. For example, many persons suffering severe neck or head trauma use a tracheostomy tube in conjunction with mechanical ventilation during extended recovery and rehabilitation periods.

Additionally, certain tracheostomy tube patients have tracheostomy tubes but are not mechanically ventilated. A number of these patients use heat and moisture exchangers in order to assist in heat and moisture control of the inhaled air. Many of these patients, like those being only mechanically ventilated, require mechanical secretion removal by use of a suction catheter.

Secretion removal is typically accomplished by a respiratory suction catheter that is advanced into and through the tracheostomy tube. As the suction catheter is withdrawn, a negative pressure or vacuum is applied to draw mucus and other secretions from the patient's airway interior of the artificial airway. While a substantial amount of mucus and other secretions will be withdrawn through the lumen of the suction catheter, a portion of the mucus and other secretions will remain as a film on the outside of the catheter.

With conventional closed suction catheter assemblies, for example as the one set forth in U.S. Pat. No. 4,569,344, which is assigned to the assignee of the present invention and is incorporated herein in its entirety for all purposes, the catheter tube is enveloped by a protective sleeve. The catheter assembly includes a valve mechanism in communication with a vacuum source to control the suctioning process. At its distal or patient end, the closed suction catheter assembly is attached to the artificial airway via a manifold, connector, adapter, or the like. When it is desired to remove secretions and mucus from the patient's respiratory tract, the catheter is advanced through the protective sleeve and into the patient's respiratory system through the artificial airway. Negative pressure is then applied to the proximal or clinician end of the catheter tube to evacuate the secretions and mucus. The tube is then withdrawn from the artificial airway and, as the catheter tube is pulled back into the protective sleeve, a wiper or seal strips or scrapes a substantial portion of any mucus or secretions from the outside of the catheter tube. However, the distal tip portion of the catheter tube may not pass through the seal or wiper and thus any secretions or mucus on the distal end must be removed by other means.

Some closed suction catheter assemblies include a lavage port for injecting a cleaning/lavage solution into a chamber at the distal end of the catheter assembly as suction is applied through the catheter tube for loosening and removing the secretions and mucus scraped from the exterior of the catheter tube. This procedure may be done with the catheter attached to or removed from the artificial airway and the ventilation circuit.

In certain situations, the lavage injection and suctioning process may not adequately remove the secretions and mucus adhering to the distal tip of the catheter tube and the clinician may repeat the cleaning process a number of times in an attempt to clean the catheter tip. If the mucus and secretions accumulate or dry on the catheter tip, they can cause infections or interfere with the suction efficiency of the catheter and necessitate premature replacement of the entire closed catheter suction assembly.

While a substantial amount of the mucus and other secretions may be withdrawn through the catheter, a portion of the mucus and other secretions remain on the outside of the catheter. Because patient's secretions can contain infectious agents, such as streptococcus, pseudonomas, staphylococcus, and HIV, it is important to shield clinicians from contact with the catheter. Likewise, it is important to shield patients from communicable pathogens in the environment and those that may be carried by the clinician. This is particularly important because patients using artificial airways often have compromised immune systems.

In normal breathing, the structures of the nose and sinus passages serve to heat and moisturize inhaled air. In situations where a patient may require mechanical ventilation on a periodic basis, it is common to place a heat and moisture exchanger (HME) on the proximal end of the artificial airway after removal of the mechanical ventilator. This type of placement is commonly done with patients who are able to breathe on their own for an extended period of time. In such systems and as used herein "proximal" refers to the direction towards the clinician and "distal" refers to the direction towards the patient.

The HME is intended to replicate the functions of heating and moisturizing air in patients having artificial airways. The HME is adapted to reduce heat and moisture loss from the respiratory system of the patient as the patient breathes. This is done by retaining the heat and moisture from air which is exhaled through the HME, and by warming and moisturizing air that is inhaled through the HME. The HME typically includes a material, such as porous foam, that is enclosed within a housing or other structure.

To date, most HMEs have not been used in conjunction with a closed suction catheter assembly. Thus, prior to suctioning respiratory secretions from a patient, it may be necessary to remove the HME from the proximal end of the artificial airway so that a suctioning catheter may be advanced to the patient's natural airways. Removal and attachment of the HME often causes discomfort to the patient and, during the period in which the HME has been removed, the patient is deprived of heat and moisture exchange and may be deprived of supplemental oxygen, if used.

Thus, there is a need for an inexpensive adapter that enables a closed suction catheter assembly that is configured to adequately remove secretions from the catheter to be easily and quickly attached to and removed from an HME that is mounted to an artificial airway while minimizing patient discomfort.

SUMMARY

Various features and advantages of the invention will be set forth in part in the following description, or may be obvious from the description, or may be learned from practice of the present invention.

The present invention provides for an endotracheal suction catheter apparatus that has a distal end. The distal end may be configured for allowing a catheter to be moved through the distal end and into the respiratory tract of a patient. The distal end defines a cleaning chamber where the catheter may be cleaned. A flap is located in the distal end and is located on one end of the cleaning chamber. The flap effects fluid flow within the cleaning chamber during cleaning of the catheter. Also, a connection member is present and is attached to the distal end. The connection member is configured for releasably engaging a heat and moisture exchanger so that the catheter may be advanced through the distal end into the heat and moisture exchanger.

Also provided according to the present invention is an embodiment of the endotracheal suction catheter apparatus as immediately discussed where an opening member is present and is disposed on the distal end or on the connection member. The opening member is configured for opening the heat and moisture exchanger when the opening member engages the heat and moisture exchanger.

The present invention also provides for a shipping plug that is used with the endotracheal suction catheter apparatus. The shipping plug has a body with an end that is configured to engage and limit the movement of the flap valve located within the endotracheal suction catheter apparatus. The body has at least one projection, and preferably four projections in an exemplary embodiment, for engaging a ridge in the endotracheal suction catheter apparatus to retain the shipping plug therein. An insertion and removal tab may be attached to the body. In a further exemplary embodiment of the present invention, the body may have a flange thereon which is used for limiting the extension of the body into the endotracheal suction catheter apparatus.

In a further exemplary embodiment of the present invention, the connection members may be a pair of arms that are pivotably attached to the distal end. Each of the arms may be provided with at least one projection for aiding engagement between the arms and the heat and moisture exchanger. In another exemplary embodiment of the present invention, each arm has two projections on one end thereof. The arms are pivotable by a user in order to engage and disengage the distal end from the heat and moisture exchanger.

Another exemplary embodiment of the present invention includes an endotracheal suction catheter apparatus as discussed above which further has a cap. The cap is engageable with the opening member when the distal end is disengaged from the heat and moisture exchanger. The cap is configured to cover at least a portion of the opening member and prevent dust and other contaminants from entering. The cap may be provided with a tether that is used for connecting the cap to the distal end. Additionally, the cap may be provided with a pull tab located on one end that is used for aiding a user in removing the cap from the opening member when the cap is engaged with the opening member.

The present invention also encompasses other exemplary embodiments that comprise combinations of features as previously mentioned. In addition, other exemplary embodiments of the present invention are defined in the claims.

BRIEF DESCRIPTION OF THE DRAWINGS

FIG. 12A is a perspective view of a cap having a tether in accordance with one exemplary embodiment of the present invention.

FIG. 12B is a front elevation view of the cap and tether shown in FIG. 12A.

FIG. 12C is a top plan view of the cap and tether shown in FIG. 12A.

FIG. 12D is a side elevation view of the cap and tether shown in FIG. 12A.

FIG. 12E is a bottom view of the cap and tether shown in FIG. 12A.

DETAILED DESCRIPTION

Figure 1:
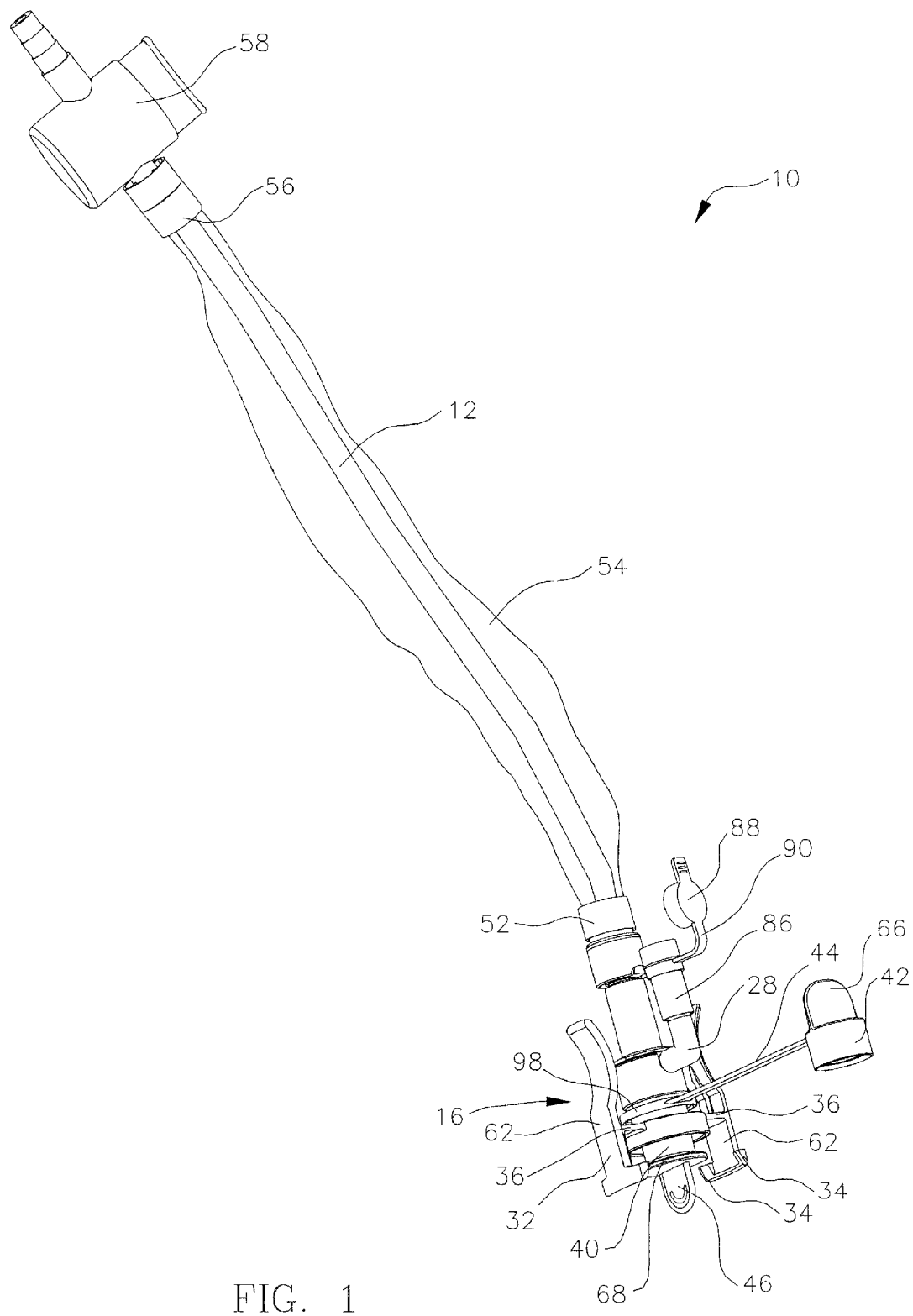
FIG. 1 is a perspective view of an exemplary embodiment of a catheter apparatus in accordance with the present invention. The catheter apparatus is shown having a shipping plug inserted into a distal end of the catheter apparatus.

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

Referring now to the drawings, an embodiment of a catheter apparatus 10 according to the invention is shown in FIG. 1. The catheter apparatus 10 includes a catheter 12 that is used for removing secretions that build up within the respiratory tract of a patient. Additionally, the catheter 12 may be used for other medical procedures in other exemplary embodiments of the present invention. The catheter 12 is surrounded by a flexible sheath 54. In one exemplary embodiment, the flexible sheath 54 is made of a flexible plastic material. The catheter 12 is made of a flexible material in order to allow for the catheter 12 to bend upon insertion and removal from the patient. Likewise, the sheath 54 may also be flexible in order to accommodate the movement of the catheter 12. The sheath 54 and the catheter 12 are sealingly and fixedly connected to a second fitting 56. The sheath 54 is fixedly attached to a first fitting 52, but the catheter 12 is slidingly engaged with the first fitting 52. The arrangement of the first fitting 52, second fitting 56, catheter 12, and sheath 54 may be as that disclosed in U.S. Pat. No. 5,715,815 which is assigned on its face to Ballard Medical Products, Inc. and is owned by the assignee of the present invention and is incorporated by reference in its entirety for all purposes. One use of sheath 54 is to protect the medical caregiver from secretions which remain on the outside of catheter 12 upon the completion of the procedure of removing secretions from a patient. Any extra secretions on catheter 12 will be contained within the sheath 54, hence isolated from the medical caregiver and also protecting the catheter 12 from outside contamination.

The catheter apparatus 10 may be provided with a pressure valve 58 that is attached to the second fitting 56. The pressure valve 58 may be configured as that shown in U.S. Pat. No. 5,664,564 which is owned by the assignee of the present invention and is incorporated herein in its entirety for all purposes. The pressure valve 58 is connected to a vacuum source (not shown) which upon actuation of both causes a vacuum to be present within the catheter 12 and hence facilitate the removal of contaminates and secretions from the patient's respiratory tract. The pressure valve 58 is in a normally closed position and can be opened by a medical caregiver when vacuum pressure is desired.

FIG. 1 shows the catheter 12 in a position in which it is not inserted into the respiratory tract of a patient. In fact, FIG. 1 shows the catheter apparatus 10 having a shipping plug 46 being inserted into the distal end 16 of the catheter apparatus 10. The shipping plug 46 is present in order to protect the interior of the catheter apparatus 10 from dirt and other contaminants before being used, and is also present in order to prevent a valve (flapper valve 20) from remaining open as will be explained in greater detail below. The catheter apparatus 10 may also be provided with a cap 42 that is connected to the distal end 16 of the catheter apparatus 10. Again, the function of the cap 42 will be explained in greater detail below.

Figure 2:
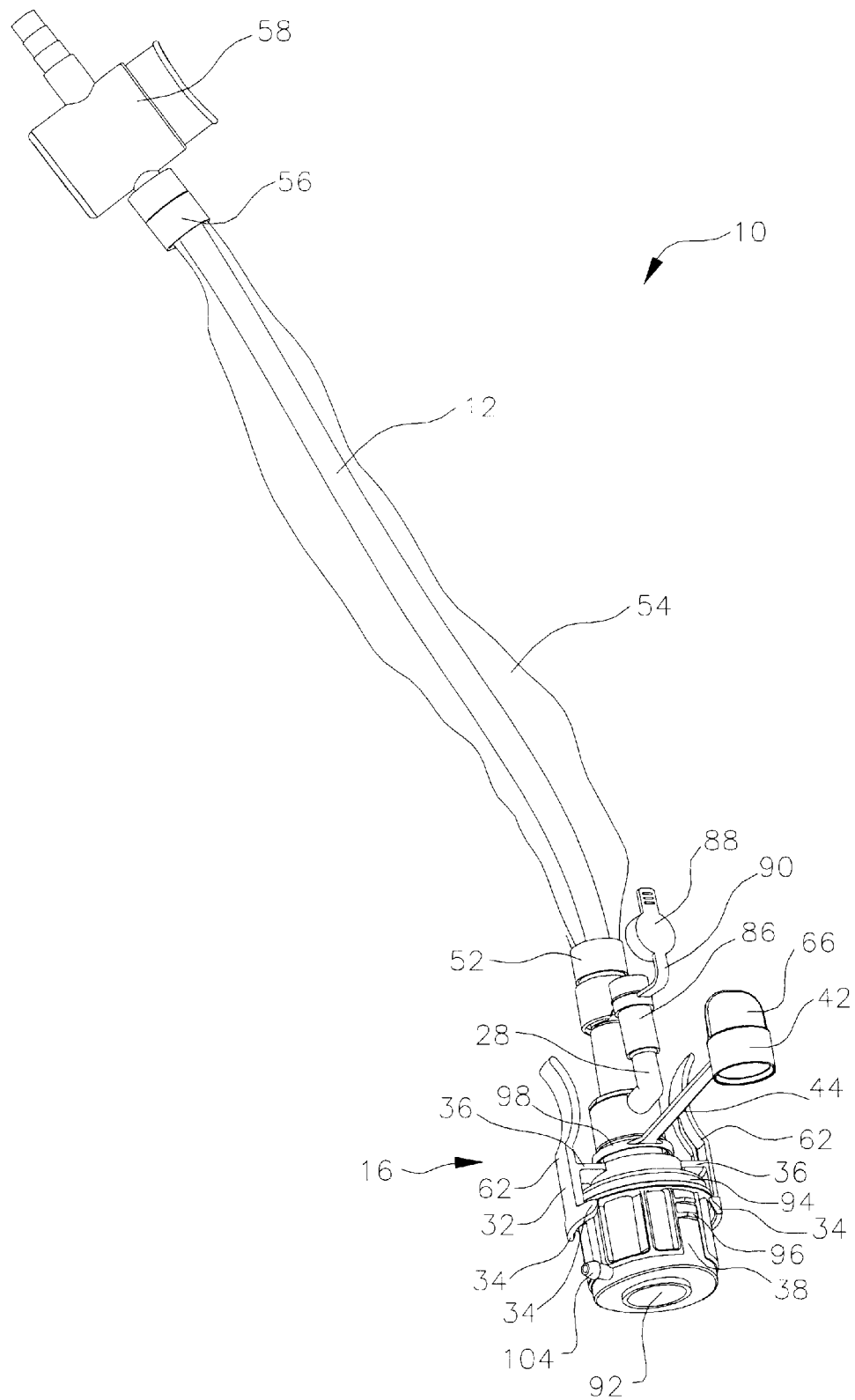
FIG. 2 is a perspective view of an exemplary embodiment of a catheter apparatus in accordance with the present invention. A heat and moisture exchanger is shown being connected to the distal end of the catheter apparatus.

The catheter apparatus 10 is also provided with a connection member 32. The connection member 32 is configured on the distal end 16 of the catheter apparatus 10. The connection member 32 may be used to attach the distal end 16 to a heat and moisture exchanger 38 as shown in FIG. 2. The connection member 32 has a plurality of projections 34 which engage a receiving ridge 94 on the heat and moisture exchanger 38 in order to retain the heat and moisture exchanger thereon. In effect, the connection member 32 allows the connection of the catheter apparatus 10 to the heat and moisture exchanger 38 such that the two components are now part of the same respiratory circuit.

Figure 8:
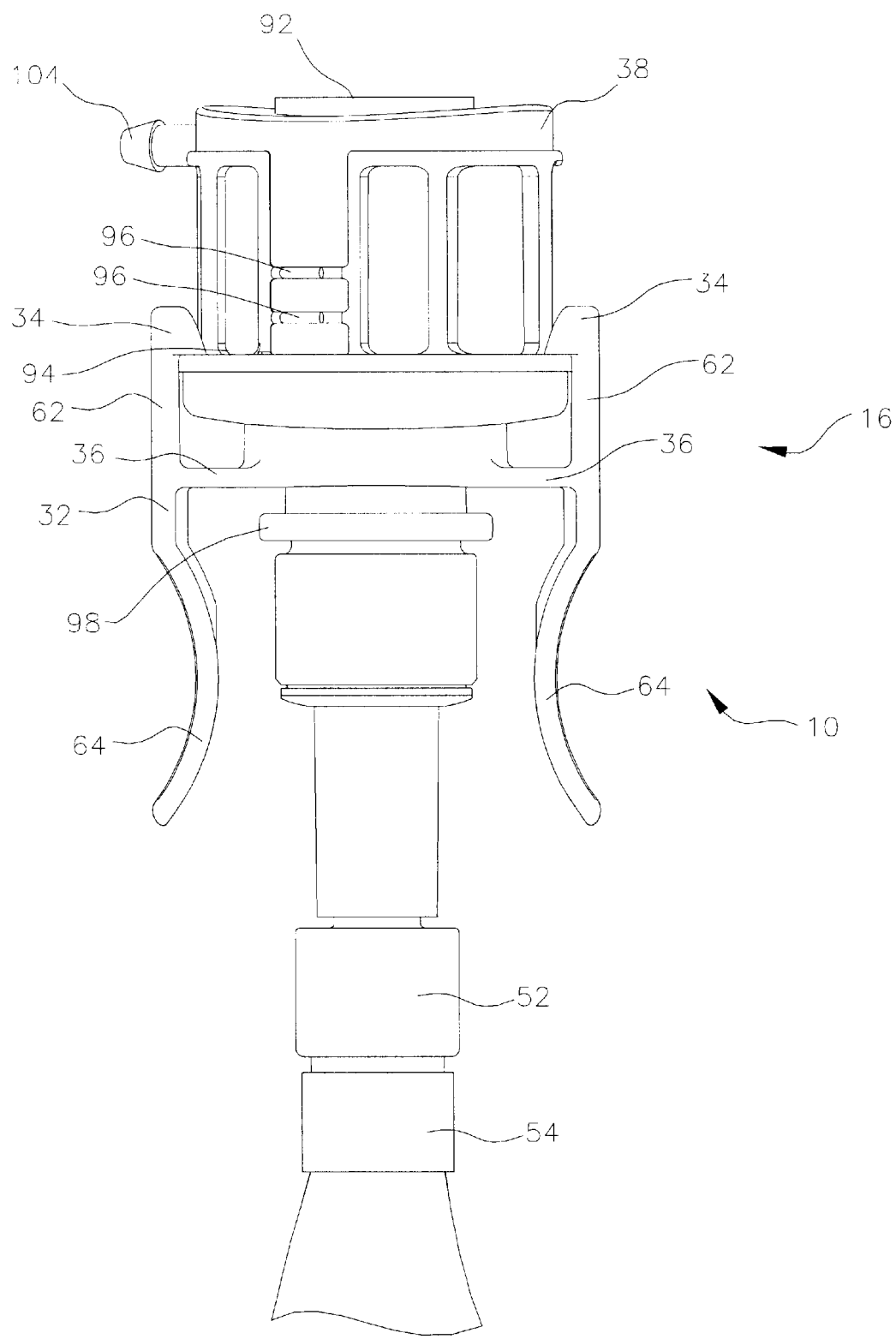
FIG. 8 is a front view of an exemplary embodiment of a catheter apparatus in accordance with the present invention. Here, the distal end is connected to a heat and moisture exchanger by a connection member.
Figure 9:
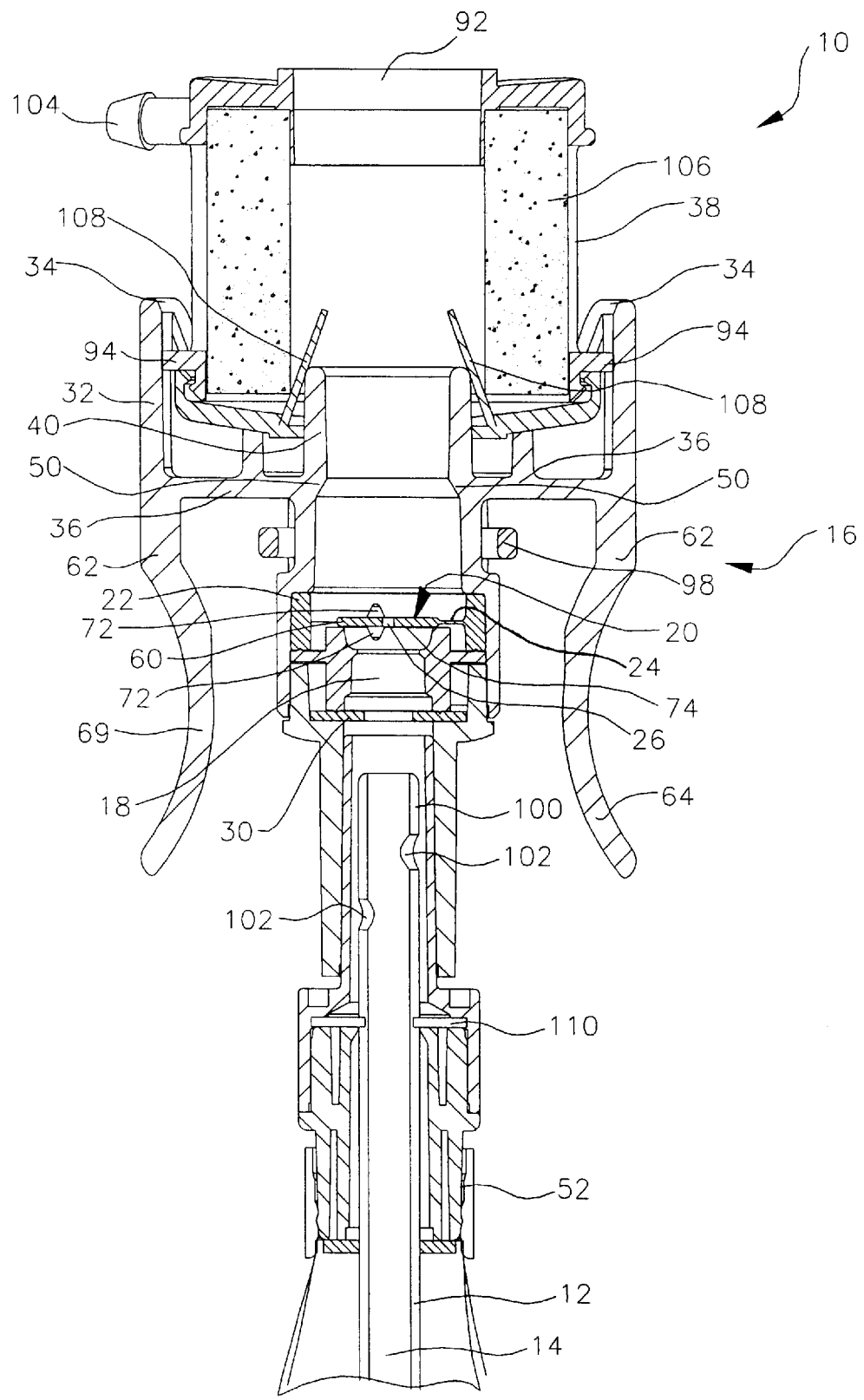
FIG. 9 is a cross-sectional view of an exemplary embodiment of a catheter apparatus in accordance with the present invention. An opening member of a connection member is shown being inserted into a heat and moisture exchanger in order to open a passageway between the heat and moisture exchanger and the distal end of the catheter apparatus.

FIG. 9 is a cross-sectional view of a portion of the catheter apparatus 10 shown in FIG. 2 and in FIG. 8. More specifically, FIG. 9 is a cross-sectional view of the distal end 16 of the catheter apparatus 10 as the heat and moisture exchanger 38 is connected thereto. The heat and moisture exchanger 38 may be configured as the one disclosed in U.S. patent application Ser. No. 09/702,376 filed on Oct. 31, 2000 and entitled "Heat and Moisture Exchanger Adaptor for Closed Suction Catheter Assembly and System Containing the Same", which is co-pending and owned by the assignee of the present invention and is incorporated herein in its entirety for all purposes. The heat and moisture exchanger 38 contains a porous material 106 that is designed to reduce heat and moisture loss as the patient breathes. Heat and moisture within exhaled air from the patient is retained within the porous material 106. The inhaled air by the patient is warmed and humidified as the inhaled air passes through and next to the porous material 106. The porous material 106 is typically made of a foam material that has sufficient porosity to reduce the loss of heat and moisture from the patient. The material may sometimes be treated with a hydroscopic salt to enhance performance. In order to effect a closed circuit, the respiratory tract of the patient is typically connected by a tube or other member to an opening in the heat and moisture exchanger passageway 92.

The heat and moisture exchanger 38 also includes a side port 104 that may be connected to an oxygen supply line in order to administer oxygen to the patient. It may be the case that oxygen is required by patients with emphysema or other ailments. Of course, in other exemplary embodiments of the present invention, the use of the side port 104 is not necessary.

Figure 14:
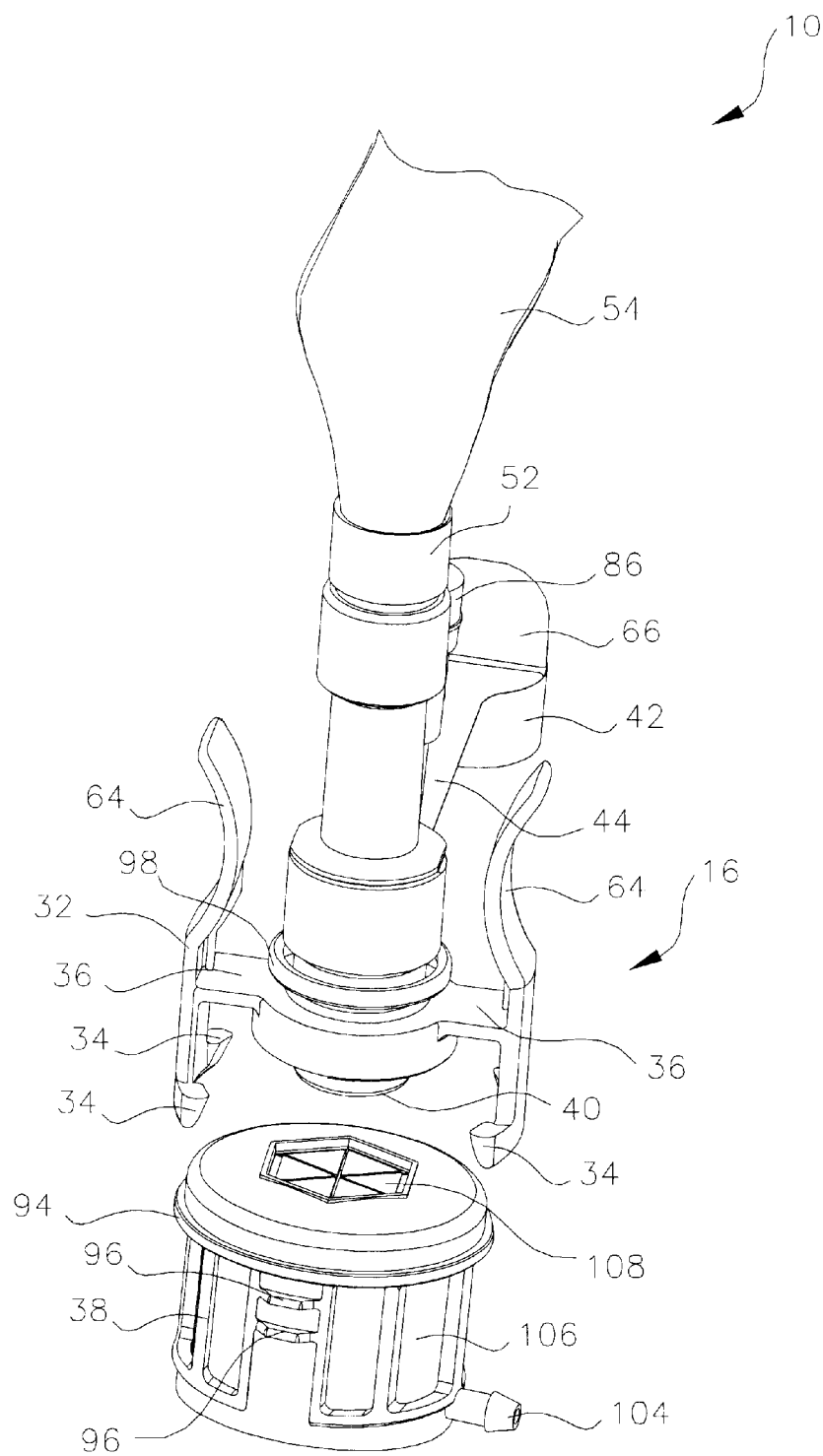
FIG. 14 is a perspective view of an exemplary embodiment of a catheter apparatus in accordance with the present invention. The catheter apparatus is disengaged from a heat and moisture exchanger that has a plurality of heat and moisture exchanger flaps which form a valve.

As can be seen in FIG. 9, an opening member 40 that is part of the connection member 32 engages and extends into the heat and moisture exchanger passageway 92. As can be seen in FIG. 14, the heat and moisture exchanger 38 is typically provided with a plurality of heat and moisture exchanger flaps 108. The heat and moisture exchanger flaps 108 form a valve whereby the heat and moisture exchanger 38 directs flow through the porous material 106 during periods when it is not engaged with the catheter apparatus 10. As can be seen in FIG. 9, the opening member 40 engages the heat and moisture exchanger flaps 108 and compresses them inward in order to create an open passageway between the catheter apparatus 10 and the heat and moisture exchanger 38. Once removed, the heat and moisture exchanger flaps 108 will return to their position shown in FIG. 14 due to the resiliency of the material from which the heat and moisture exchanger flaps 108 is constructed.

Figure 3:
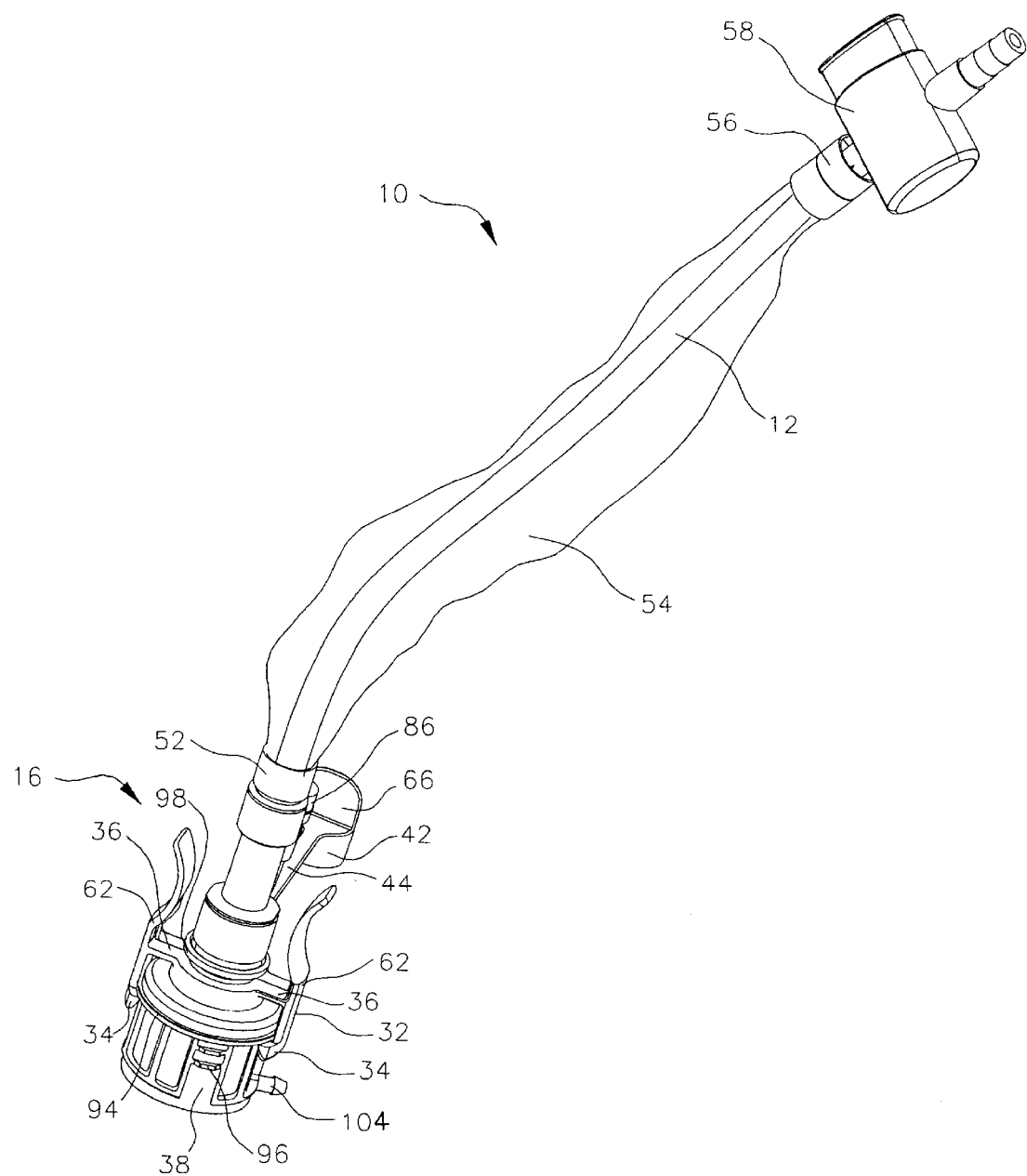
FIG. 3 is a perspective view of the catheter apparatus shown in FIG. 2. Here, another side of the catheter apparatus is shown from that shown in FIG. 2.

Therefore, FIG. 14 shows the catheter apparatus 10 as being in a situation immediately prior to engaging or immediately after disengaging from the heat and moisture exchanger 38. The attachment of the heat and moisture exchanger 38 to the catheter apparatus 10 may be seen in FIGS. 2 and 3 which show different views of the attachment between these two components.

Figure 4:
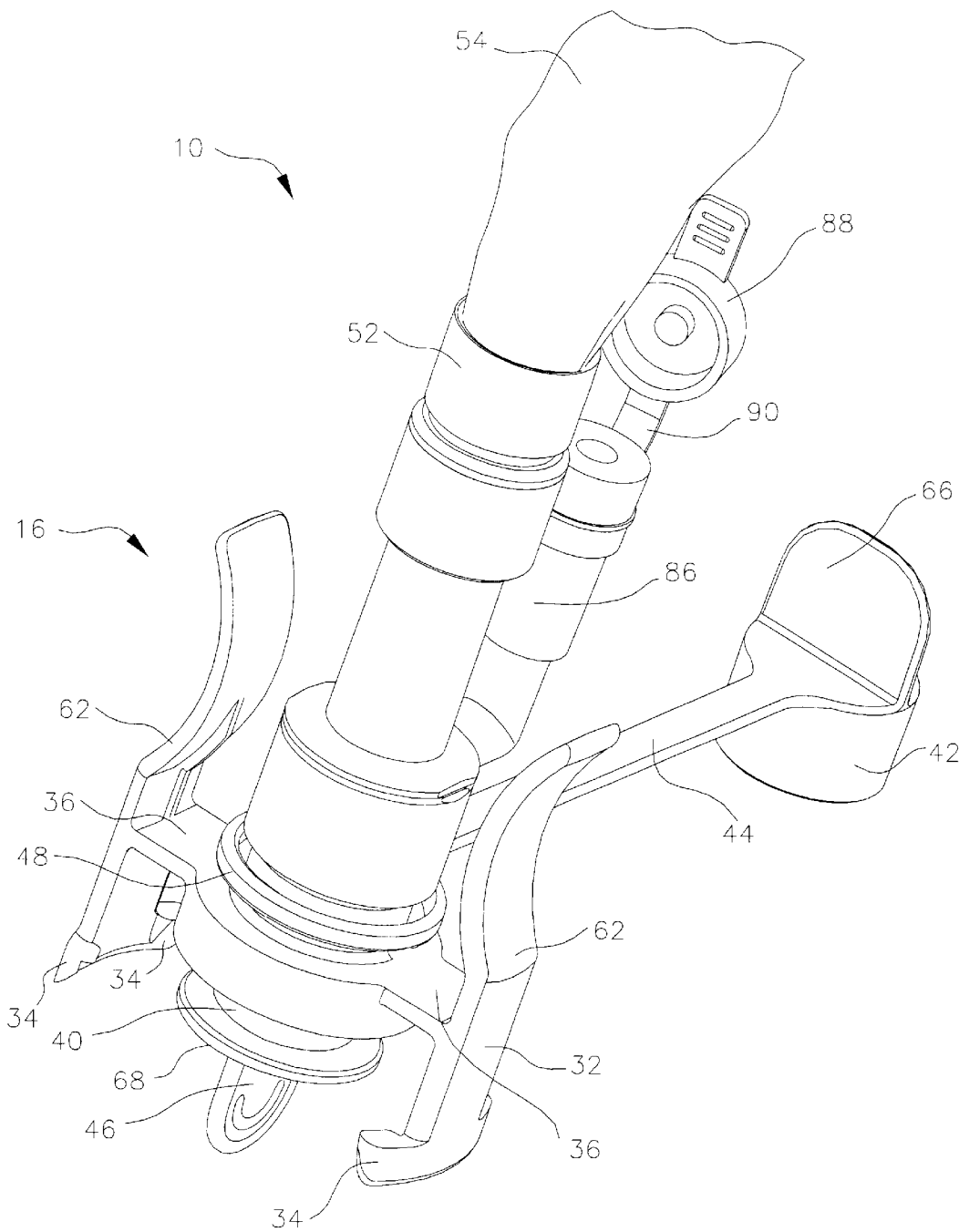
FIG. 4 is a close-up perspective view of an exemplary embodiment of a catheter apparatus in accordance with the present invention. The distal end of the catheter apparatus is shown having the shipping plug inserted therein.
Figure 5:
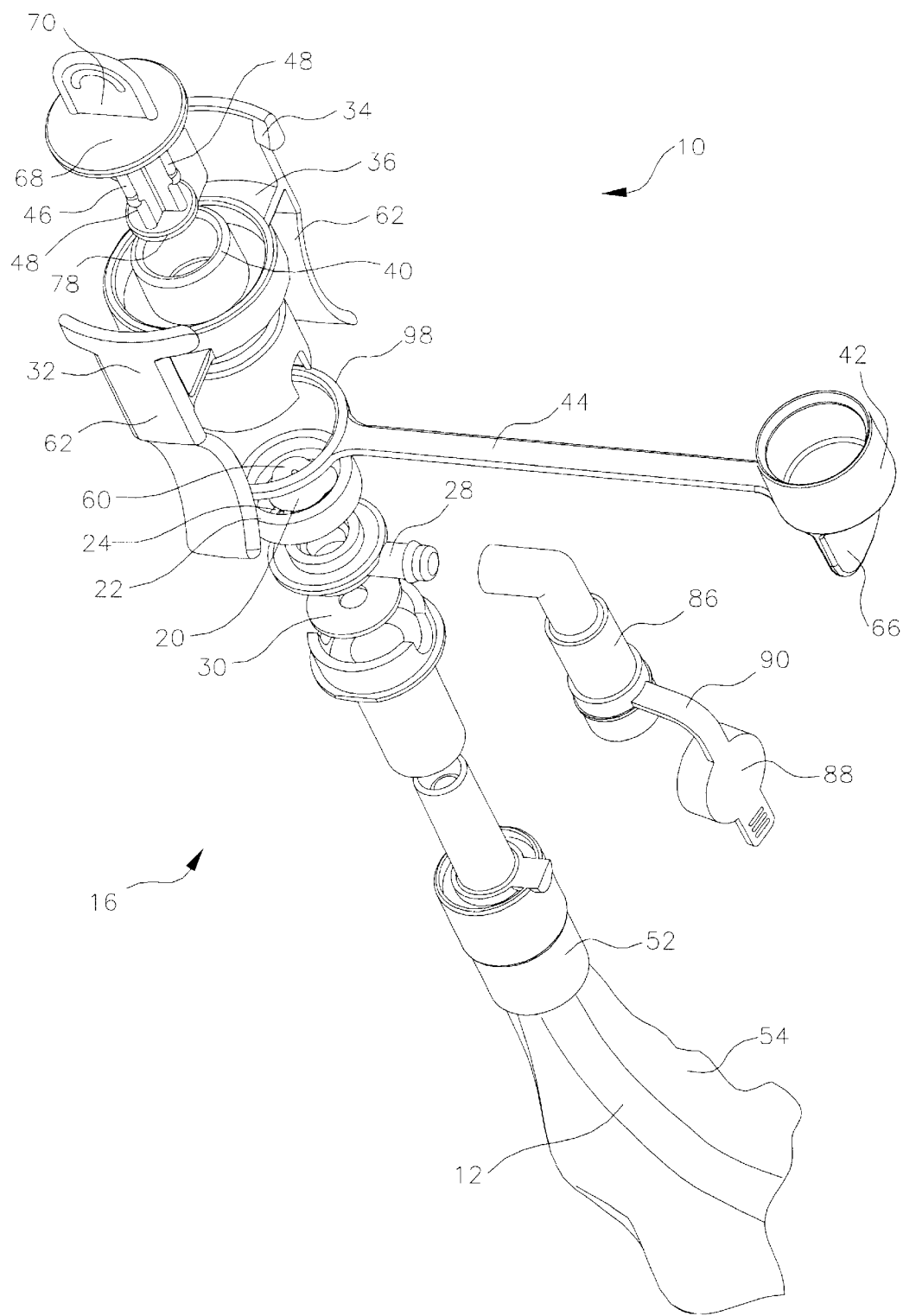
FIG. 5 is an exploded assembly view of the catheter apparatus shown in FIG. 4. The view shows a valve, a shipping plug, a wiper seal, and other components that are on the distal end of the catheter apparatus.
Figure 6:
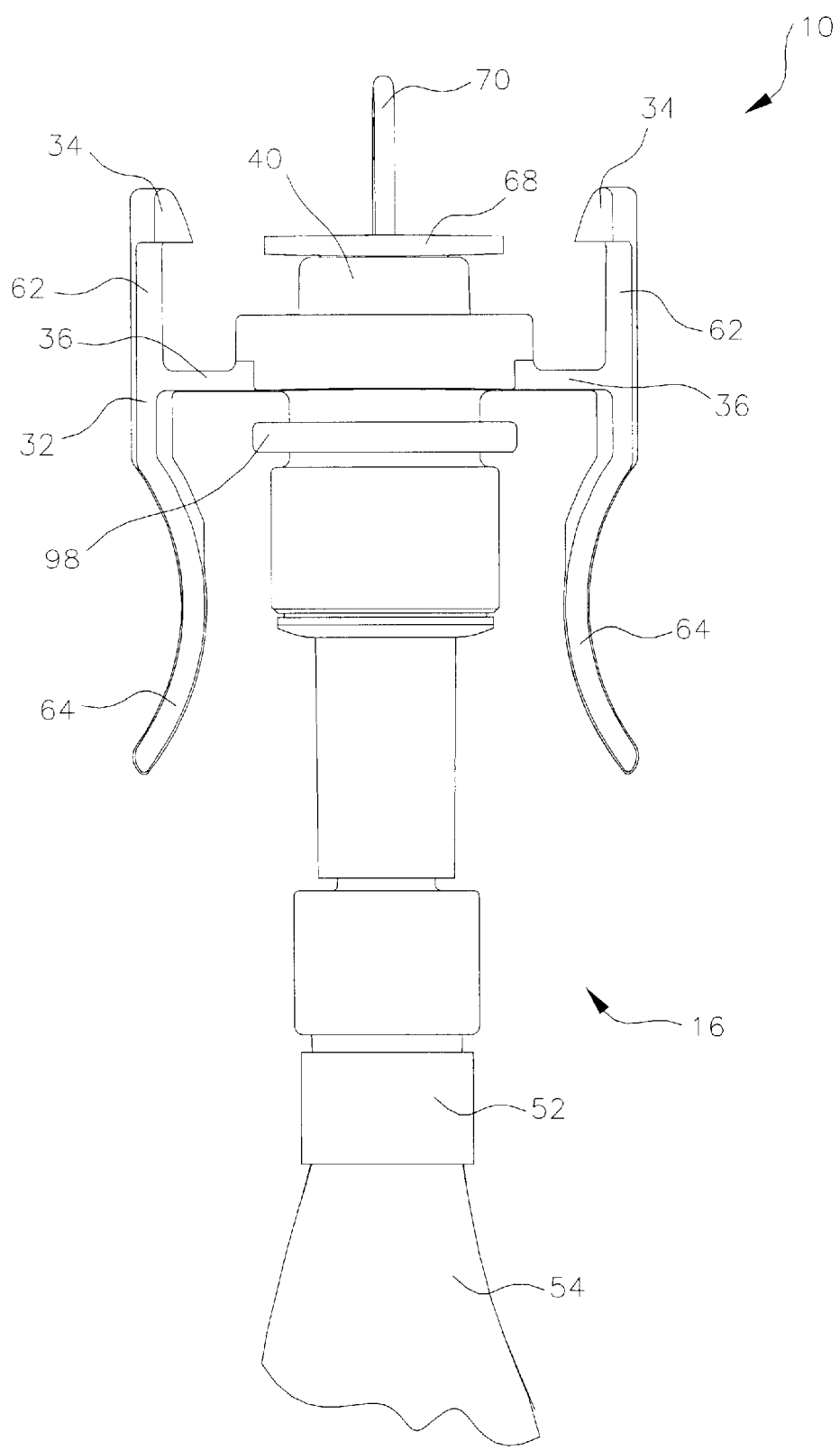
FIG. 6 is a front elevation view of a catheter apparatus in accordance with an exemplary embodiment of the present invention. The view shows a close-up of the distal end of the catheter apparatus having a shipping plug.
Figure 7:
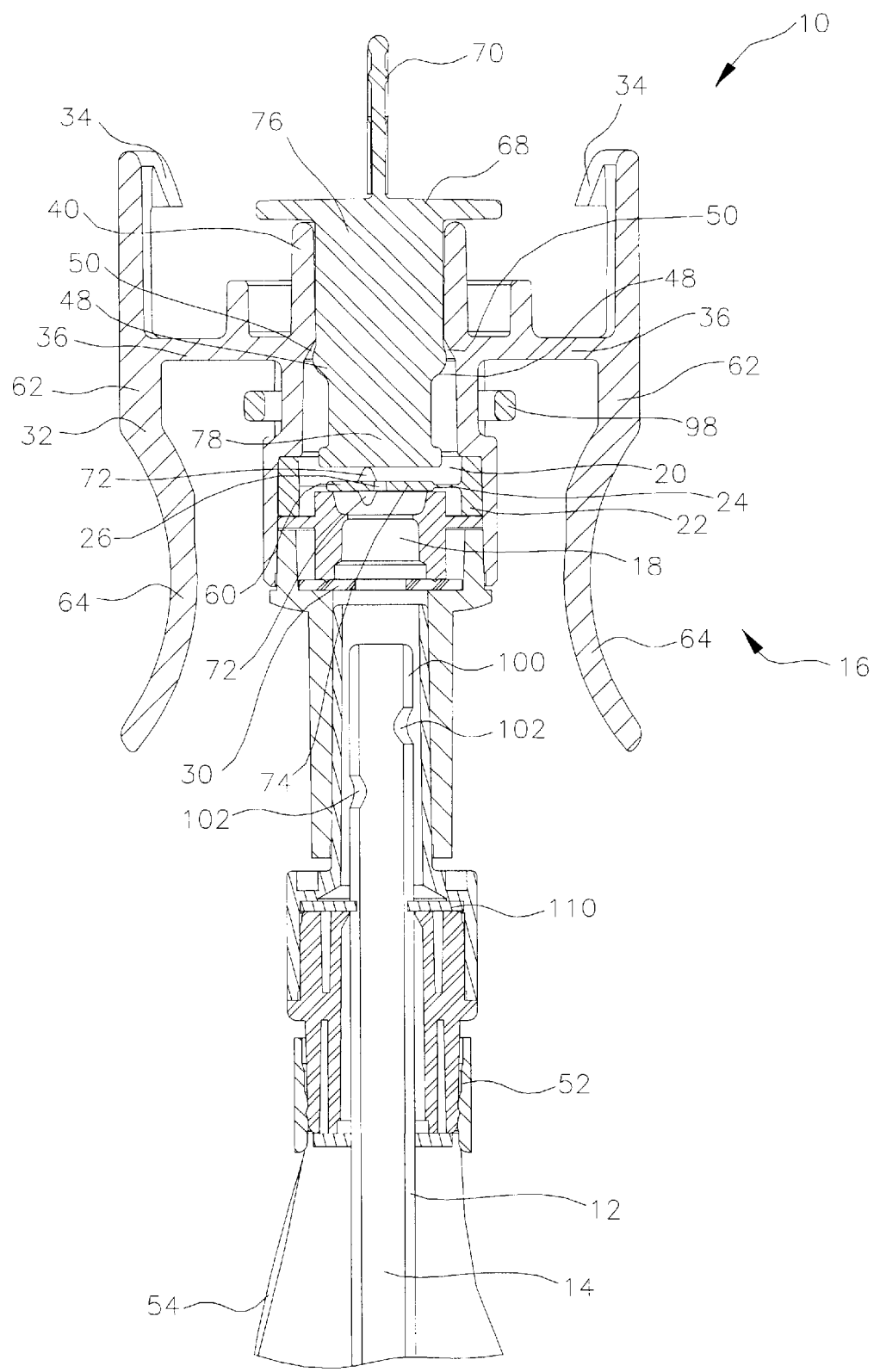
FIG. 7 is a cross-sectional view of an exemplary embodiment of a catheter apparatus in accordance with the present invention. The view shows a shipping plug being inserted into the distal end of the catheter apparatus and limiting forward movement of a valve hingedly attached within the distal end.

FIG. 7 is a cross-sectional view of the catheter apparatus 10 which has the shipping plug 46 inserted into the distal end 16. FIG. 6 is a front view of the catheter apparatus 10 with the shipping plug 46. FIG. 5 is an exploded assembly view of the catheter apparatus 10 shown in FIGS. 4 and 7. As can be seen in FIGS. 5 and 7, the catheter apparatus 10 is provided with a valve 20 in the distal end 16. In one exemplary embodiment of the present invention, valve 20 may be in the form of a flap 60. However, it is to be understood that other configurations of the valve 20 are possible in other exemplary embodiments of the present invention. The flap 60 may be connected to an annular ring 22 by one or more hinges 24. The annular ring 22 is in-turn rigidly connected to a portion of the distal end 16. Again, in other exemplary embodiments of the present invention the flap 60 may be connected immediately to the distal end 16 without the use of the annular ring 22. Also, the valve 20 may be configured as disclosed in U.S. Pat. No. 6,227,200 B1 which is owned by the assignee of the present invention and is incorporated herein in its entirety for all purposes.

The valve 20 forms an end of a cleaning chamber 18 that is located within the distal end 16. The cleaning chamber 18 may be defined as being located between the valve 20 on one end and a second wiper seal 110 on the other in one exemplary embodiment of the present invention. The cleaning chamber 18 may be in communication with a port 28 as shown in FIGS. 5 and 2. Port 28 may be attached to a lavage connection member 86. Cleaning solution may be injected through the lavage connection member 86 and enter the cleaning chamber 18 through port 28. The lavage connection member 86 is connected to a cap 88 by a tether 90. The purpose of the cap 88 is to cover an opening in the lavage connection member 86 when the lavage connection member 86 is not being used. This coverage protects the catheter apparatus 10 and in particular the ravage connection member 86 from dirt and other contaminants.

The port 28 is not present in FIG. 7 due to the fact that FIG. 7 is a cross-sectional view. However, it can be appreciated from study of at least FIGS. 2 and 5 that the cleaning chamber 18 may be in fluid communication with the port 28 in FIG. 7. As such, the catheter 12 may be advanced into the cleaning chamber 18 such that a distal tip 100 of the catheter 12 is proximate to but not in contact with wiper seal 30. The catheter 12 may also be provided with a pair of side apertures 102 as shown in FIG. 7. As previously mentioned, the catheter 12 will be in need of periodic cleaning due to its contact with the respiratory tract of the patient. Cleaning solution may be injected into the cleaning chamber 18 and suction may be applied to a lumen 14 of the catheter 12 such that secretions and other contamination are drawn through the lumen 14 and out of the catheter apparatus 10.

As such, the catheter apparatus 10 may be designed to be intermittently attached to the tracheal path of a patient when cleaning is required. The catheter apparatus 10 is specifically designed to be in communication with the heat and moisture exchanger 38. Once suctioning of the patient is completed, the catheter 12 may be cleaned. The catheter apparatus 10 may be used to remove secretions from patients that are not mechanically ventilated and are using a tracheal heat and moisture exchanger 38. The catheter 12 may be cleaned in the cleaning chamber 18 either before or after the distal end 16 has been disconnected from the heat and moisture exchanger 38.

The distal end 16 may also be provided with a wiper seal 30 as shown in FIG. 7. The purpose of wiper seal 30 is to remove secretions from the outer surface of catheter 12 as the catheter 12 is advanced back through the wiper seal 30. The wiper seal 30 may be made of a flexible material that sealingly engages the catheter 12 as the catheter 12 is retracted from the distal end 16 of the catheter apparatus 10. However, it may be the case that secretions remain on the catheter 12 even after passing through the wiper seal 30 and remain on the catheter 12 after passing through the first fitting 52. These secretions are prevented from contacting the clinician or the environment due to the presence of the sheath 54. The distal end 16 may be provided with the second wiper seal 110 that functions similarly to the wiper seal 30. In addition, this second wiper seal 110 may be located in the first fitting 52 to form a double positive and expiratory pressure seal along with the flap 60.

As can be seen in FIG. 7, the catheter 12 is present within the cleaning chamber 18, as in this exemplary embodiment the cleaning chamber 18 is defined as being between the flap 20 and the second wiper seal 110. A cleaning procedure may be commenced. In order to clean the catheter 12, cleaning solution is injected into the cleaning chamber and suction is applied to the lumen 14 of the catheter 12. The cleaning solution will act to break up secretions that are present on the distal tip 100 of the catheter 12 and also on the outside of the catheter 12 walls. In-turn, the suctioning imparted on the lumen 14 will draw these secretions into the catheter 12 and remove them from the catheter apparatus 10. Once suction is applied to the lumen 14, the valve 20 which consists of the flap 60 will be drawn towards the catheter 12 and away from the patient. The flap 60 may be provided with an aperture 26. As discussed in U.S. Pat. Ser. No. 09/741,769 filed on Dec. 19, 2000 and entitled "Turbulent Air Cleaning Method and Apparatus for Catheter Assemblies" which is co-pending and owned by the assignee of the present invention and is incorporated herein in its entirety for all purposes, a turbulent airflow may be created within the cleaning chamber 18.

The suction force applied to the lumen 14 serves to draw the cleaning solution into the opening of the distal tip 100 and establish the turbulent airflow path. When suction is applied, a fluid medium other than the cleaning solution (in this case air) is drawn through the aperture 26 and into the distal tip 100 with the cleaning solution. Although not wishing to be bound by any theory of operation, the Applicants believe that in this type of turbulent flow cleaning method, a portion of the air and cleaning solution mixture is then directed out of the side apertures 102 and travels along the outer circumferential surface of the catheter 12 and is drawn back into the distal tip 100. Thus, a continuous circular flow path or pattern is established. It has been found that this pattern causes a significant turbulence in the cleaning solution around the outer circumference of the catheter 12. This turbulence greatly enhances the cleaning effect of the cleaning solution.

The aperture 26 may be axially aligned with the catheter 12 during cleaning procedures. Additionally, flap projections 72 may be provided so that a planar surface 74 of the flap 60 does not seal against the catheter 12 as suction is applied. Preferably, the distal tip 100 of the catheter 12 is placed a slight distance below the wiper seal 30 during cleaning procedures. The port 28 may be located below wiper seal 30 such that cleaning solution is directed onto the outer circumference of the catheter 12 to assist in cleaning. Suctioning may be applied to the lumen 14 of the catheter 12 until all of the saline has been evacuated from the cleaning chamber 18 and the catheter 12 is cleaned. The cap 42 may be placed over the opening member 40 in the connection member 32 and the catheter apparatus 10 may be stored until another suctioning is required.

A turbulent airflow may be created within the cleaning chamber 18 by use of the aperture 26 along with the side apertures 102 of the catheter 12. By having such an arrangement, a more effective cleaning process will be realized in the catheter apparatus 10. However, it is to be understood that in other exemplary embodiments of the present invention, the cleaning process need not be carried out as previously mentioned. For instance, in other exemplary embodiments of the present invention the aperture 26 may not be present in the flap 60. Additionally, the side apertures 102 need not be present in the catheter 12 in other exemplary embodiments. Further, the size and shape of the cleaning chamber 18 may be modified in other exemplary embodiments of the present invention, along with the presence or non-presence of the wiper seal 30.

The flap 60 may be provided with a pair of flap projections 72. Insertion of the catheter 12 through the distal end 16 will cause the flap 60 to open due to the force of the distal tip 100. In order to prevent the distal tip 100 from transferring secretions or other contaminations onto the flap 60, the flap 60 is provided with the flap projection 72 in order to engage the catheter 12. As such, when inserted through the distal end 16, the catheter 12 will engage the flap projection 72 and not contact a planar surface 74 of the flap 60. The use of projection 72 therefore reduces the risk of contamination in the catheter apparatus 10. However, in other exemplary embodiments of the present invention, the flap 60 is not provided with the flap projections 72.

Figure 11B:
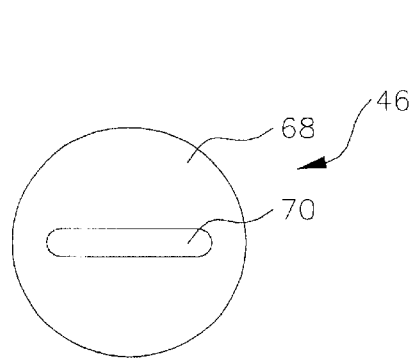
FIG. 11B is a top plan view of the shipping plug shown in FIG. 11A.
Figure 11A:
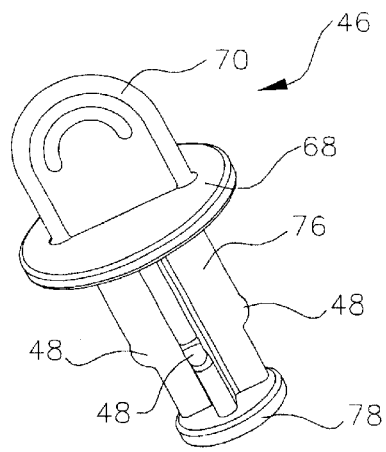
FIG. 11A is a perspective view of a shipping plug in accordance with one exemplary embodiment of the present invention.
Figure 11C:
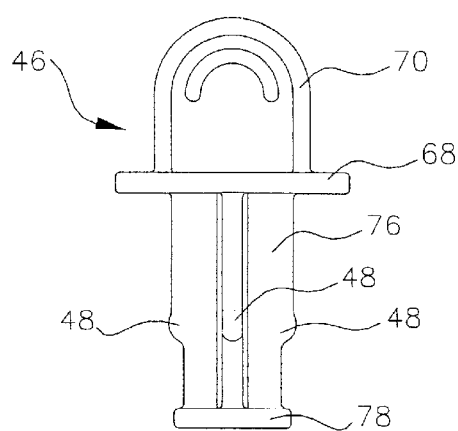
FIG. 11C is a front elevation view of the shipping plug shown in FIG. 11A.
Figure 11D:
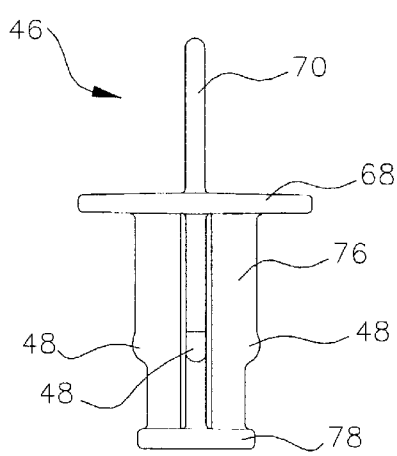
FIG. 11D is a side elevation view of the shipping plug shown in FIG. 11A.
Figure 11E:
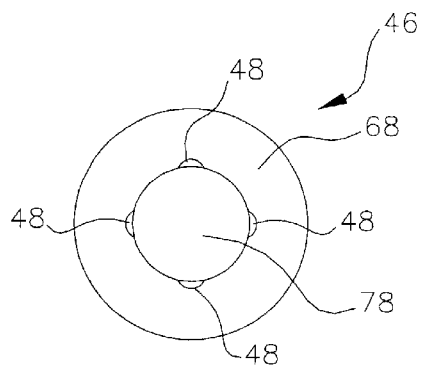
FIG. 11E is a bottom view of the shipping plug shown in FIG. 11A.
Figure 13B:
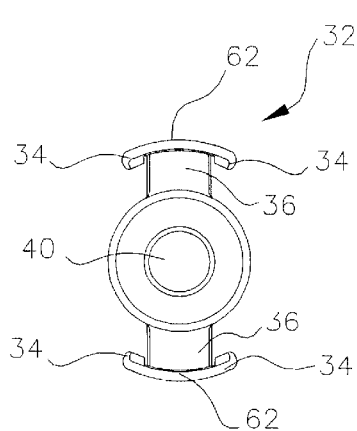
FIG. 13B is a top plan view of the connection member shown in FIG. 13A.
Figure 13C:
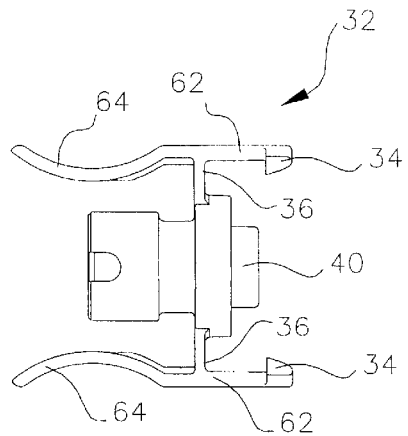
FIG. 13C is a side elevation of the connection member shown in FIG. 13A.
Figure 13D:
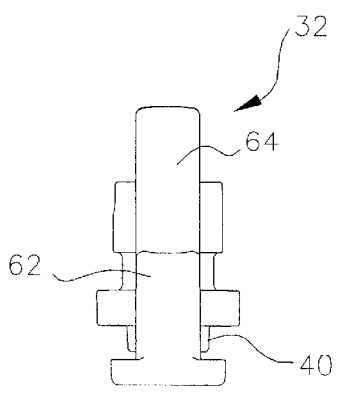
FIG. 13D is a front elevation view of the connection member shown in FIG. 13A.
Figure 13A:
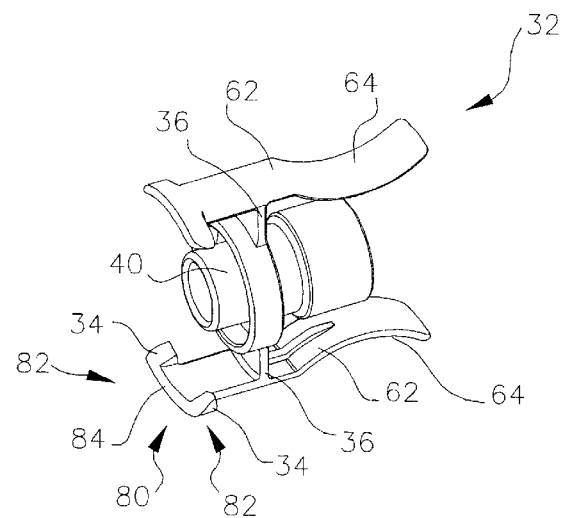
FIG. 13A is a perspective view of a connection member in accordance with one exemplary embodiment of the present invention.

It may be the case that during periods of non-use, especially during periods of shipment from the manufacturer to eventual use by the clinician, the catheter 12 may move into the distal end 16 such that the valve 20 is opened. The valve 20 and the hinge 24 are constructed of a flexible plastic material. If this material were to remain in one position for an extended period of time, it may be the case that the material will set and hence the valve 20 will remain in the open position even when the catheter 12 is removed from the distal end 16. If the plastic forming the hinge 24 were to set due to a prolonged period of being open, there is a potential that the valve 20 will not close when cleaning of the catheter 12 is performed. Obviously, such a situation is not desired when the catheter 12 is withdrawn and the catheter apparatus 10 is or is not connected to the respiratory tract of a patient. In order to keep the valve 20 closed during periods of non-use, and especially during shipment to the end user, the catheter apparatus 10 is provided with the shipping plug 46. The shipping plug 46 is shown in detail in FIGS. 11A through 11E. Although stated in the drawings section as having a top, front, side, and bottom, it is to be understood that these descriptions are being made for ease of convenience. In fact, all such descriptions in the drawings section concerning other figures are also made for sake of convenience. Here, the shipping plug 46 is provided with a body 76 that has four projections 48 extending therefrom. On one end of the body 76 is an end 78. End 78 is shown in FIG. 11A as being a substantially circular disk. On another end of the body 76 an insertion and removal tab 70 may be placed. A flange 68 is proximate to the insertion and removal tab 70.

FIG. 7 shows the shipping plug 46 being inserted into the distal end 16 of the catheter apparatus 10. The end 78 is positioned such that the valve 20 may not open due to the contact of the flap projection 72 on the valve 20 with the end 78. In other exemplary embodiments of the present invention, the end 78 may contact portions of the valve 20 other than the flap projection 72. Because the end 78 impedes movement of the valve 20, the valve 20 will not become opened during shipment of the catheter apparatus 10 due to the presence of the shipping plug 46.

In order to retain the shipping plug 46 in the distal end 16, the shipping plug 46 may be provided with the four projections 48. These projections 48 are resilient members which will compress upon the insertion of the shipping plug 46 into the distal end 16. Once the projections 48 pass a ridge 50 that is formed on the inside of the distal end 16, the projections 48 will spring back and secure the shipping plug 46 within the distal end 16 with a determined amount of force. The projections 48 of the shipping plug 46 are specifically designed to lock the shipping plug 46 into the distal end 16 with enough retention force to prevent the valve 20 from opening. FIG. 7 shows the ridge 50 being formed on an inside portion of the connection member 32. However, it is to be understood that in other exemplary embodiments of the present invention, the ridge 50 may be formed on other portions of the distal end 16 besides the connection member 32. In an exemplary embodiment of the present invention, the shipping plug 46 has four projections 48. However, it is to be understood that the shipping plug 46 may be provided with any number of projections 48. In addition, other configurations of retaining the shipping plug 46 within the distal end 16 are envisioned under the present invention. For instance, an interference fit between the body 76 of the shipping plug 46 and the inner passageway of the distal end 16 is possible.

The shipping plug 46 may be provided with the flange 68 in order to limit the inward movement of the shipping plug 46 into the distal end 16. Also, the flange 68 may be sized such that it prevents a user from inadvertently inserting the shipping plug 46 into the heat and moisture exchanger 38. The shipping plug 46 is provided with the insertion and removal tab 70 in order to aid a user in inserting the shipping plug 46 into the distal end 16 and for removing the shipping plug 46 from the distal end 16. Once the catheter apparatus 10 is purchased by a user and ready for use, the shipping plug 46 may be removed from the distal end 16 and discarded, unless the catheter apparatus 10 is to be stored for a long period of time between uses.

Figure 10:
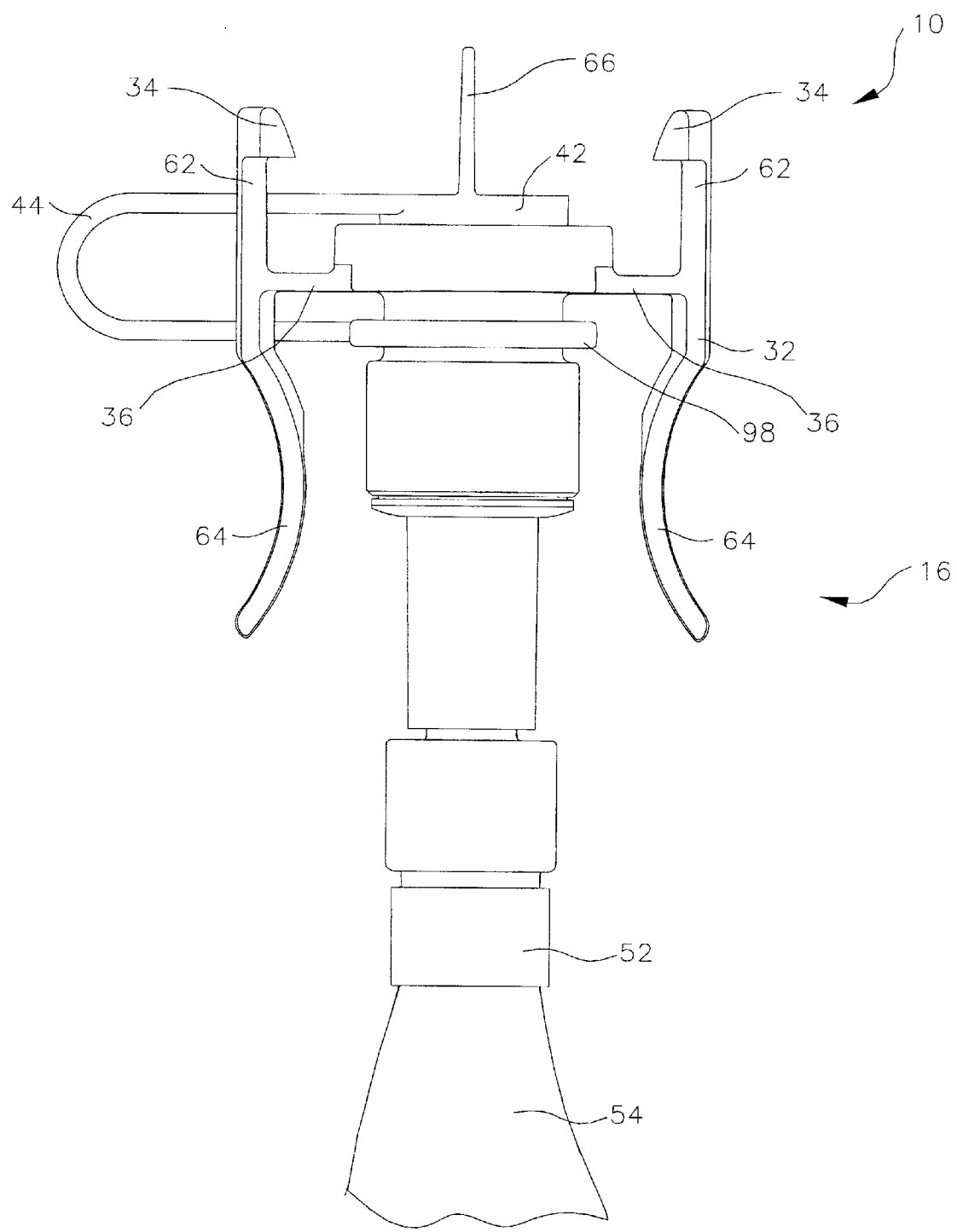
FIG. 10 is a front elevation view of a catheter apparatus in accordance with an exemplary embodiment of the present invention. Here, the catheter apparatus is not connected to a heat and moisture exchanger and a cap is placed over the distal end.

The catheter apparatus 10 shown in FIG. 5 is provided with a cap 42. The purpose of cap 42 is to cover the opening member 40 when the catheter apparatus 10 is not being used. This covering prevents the opening member 40 from being subjected to dirt and other contaminants which can enter the catheter apparatus 10. Although shown as part of the connection member 32 in FIG. 5, opening member 40 may be connected to or formed on other portions of the distal end 16 in other exemplary embodiments of the present invention. FIG. 10 shows the cap 42 being placed on the catheter apparatus 10 during a period of non-use of the catheter apparatus 10. As such, the distal end 16 is protected from dirt and other contaminants. The cap 42 is connected to the distal end 16 by a loop 98. FIGS. 12A through 12E show the cap 42 in greater detail. The cap 42 is connected to the loop 98 by way of a flexible tether 44. However, it is to be understood that in other exemplary embodiments of the present invention, the tether 44 is not present, and the cap 42 is simply a member that is not connected to the distal end 16. Additionally, other ways of connecting the tether 44 to the distal end 16 may be envisioned which do not require the use of the loop 98. For instance, the tether 44 can be pinned or bolted to the distal end 16. In addition, in other exemplary embodiments of the present invention, the cap 42 may be connected to the catheter apparatus 10 at a location other than the distal end 16. The cap 42 is provided with a pull tab 66 that aids a user in placing the cap 42 on the opening member 40 and removing the cap 42 from the opening member 40.

As shown in FIG. 8, the connection member 32 is used to connect the catheter apparatus 10 to the heat and moisture exchanger 38 so that a flow path therethrough is created. The opening member 40 as seen in FIG. 9 is provided in order to open a passageway through the heat and moisture exchanger flaps 108. This type of an arrangement is advantageous in that if the heat and moisture exchanger flaps 108 were opened by insertion of the catheter 12, mucus and other secretions on the catheter 12 would be deposited onto the heat and moisture exchanger flaps 108 upon the withdrawal of the catheter 12 from the respiratory tract. By providing the opening member 40 that can open the heat and moisture exchanger flaps 108, a reduced risk of contamination is present because the catheter 12 does not have to contact any portion of the heat and moisture exchanger 38. It is to be understood that in other exemplary embodiments of the present invention, the heat and moisture exchanger 38 may be placed in communication with the catheter apparatus 10 where the heat and moisture exchanger flaps 108 are not opened by the opening member 40.

The connection member 32 engages the heat and moisture exchanger 38 and holds the heat and moisture exchanger 38 onto the distal end 16. The connection member 32 is shown in greater detail in FIGS. 13A through 13D. The references to the connection member 32 having a front, top, and side view in the drawings section were made for ease of convenience. The connection member 32 is provided with a pair of arms 62. The projections 34 are present on one end of the arms 62. In other exemplary embodiments of the present invention, the projections 34 may be a barb 82. Further, a surface member 80 may be present on one end of an arm 62 and is configured for grasping the heat and moisture exchanger 38. In one exemplary embodiment, the surface member 80 is a flange 84 that is used to help retain or retain by itself the distal end 16 to the heat and moisture exchanger 38. As such, the present invention includes exemplary embodiments where the connection is effected by members other than the projections 34 as shown in the drawings.

The arm 62 is displaceable with respect to a portion of the connection member 32 proximate to the opening member 40. In one exemplary embodiment, the arm 62 is pivotably attached to the connection member 32. This pivotable connection is effected by a pivot attachment 36. The pivot attachment 36 is a flexible piece of material that allows for the arms 62 to flex away from and towards the opening member 40. As such, the projections 34 will also flex away from or towards the opening member 40. The pivotable attachment 36 may be a material that is rigid yet flexible enough to allow for this pivoting action to occur. In order to aid a user in pivoting the arms 62, the arms 62 may each be provided with a curved finger tab 64. Therefore, a user may place his or her thumb and index finger against the curved finger tab 64 and pivot the arms 62 such that the projections 34 are away from the opening member 40. At this point, the connection member 32 may be advanced over the heat and moisture exchanger 38 as shown in FIG. 9. Upon removing pressure from the arms 62, they will move back into their natural position which causes the projections 34 to engage the receiving ridge 94 of the heat and moisture exchanger 38 and retain the catheter apparatus 10 thereon. In addition, the arms 62 may be biased towards one another such that when placed over the heat and moisture exchanger 38, they more securely engage the heat and moisture exchanger 38. As shown in FIG. 14, the heat and moisture exchanger 38 may also be provided with a series of receiving projections 96. As such, the arms 62 of the connection member 32 may be connected to the receiving projections 96 instead of the receiving ridge 94 in other exemplary embodiments of the present invention. In addition, the receiving projections 96 may be used to engage a connection member 32 that has a locking slot onto which the heat and moisture exchanger 38 may be retained. Such an arrangement is shown in the aforementioned Patent Application "Entitled Heat and Moisture Exchanger Adaptor for Closed Suction Catheter Assembly and System Containing the Same" having Ser. No. 09/702,376.

In order to remove the distal end 16 from the heat and moisture exchanger 38, a user may again place his or her thumb and index finger on the curved finger tabs 64 and depress them inwards. This will again cause the projections 34 to pivot outwards with respect to the pivotable attachments 36. Clearance of the projections 34 from the receiving ridge 94 will be attained and the connection member 32 may be successfully disengaged from the heat and moisture exchanger 38.

It should be understood that the present invention includes various modifications that can be made to exemplary embodiments of the catheter apparatus described herein as come within the scope of the appended claims and their equivalents.

What is claimed is:

1. An endotracheal suction catheter apparatus comprising:
   a catheter configured for removing fluids from a respiratory tract of a patient by applying negative pressure to a lumen of said catheter;
   a distal end configured to allow said catheter to be moved through said distal end and into the respiratory tract of a patient, said distal end having a cleaning chamber in which said catheter may be cleaned;
   a valve disposed in said distal end and proximate to said cleaning chamber so as to pivot with respect to an annular ring, said valve being a flap attached to said annular ring, said flap having an aperture therein;
   a port in fluid communication with said cleaning chamber for introducing a cleaning solution into said cleaning chamber;
   a wiper seal located in said cleaning chamber, said wiper seal configured for removing secretions on said catheter as said catheter is advanced past said wiper seal;
   a connection member being a pair of arms attached to said distal end, each of said arms having at least one projection, said arms configured for engaging and securing said distal end to a heat and moisture exchanger;
   an opening member disposed on one end of said distal end, said opening member configured for opening the heat and moisture exchanger when said distal end is engaged and secured to the heat and moisture exchanger;
   a cap attached to said distal end by a tether, said cap configured for engaging said opening member and covering said opening member when said endotracheal suction catheter is not being used;
   a shipping plug configured for engaging said opening member and extending into said distal end such that said shipping plug limits movement of said valve, said shipping plug having a plurality of projections which engage a ridge in said distal end and act to lock said shipping plug on said distal end;

a first fitting connected to said distal end and immediately adjacent to said wiper seal, said first fitting slidably joined to said catheter;

a sheath connected on one end to said first fitting and forming a single enclosed area that concentrically surrounds said catheter, said sheath being collapsible when said catheter is inserted into the respiratory tract of a patient;

a second fitting attached to said sheath on an opposite end of said sheath from said first fitting, said second fitting non-slidably joined to said catheter; and a normally closed pressure valve connected to said second fitting, actuation of said pressure valve allowing negative pressure to be supplied to said catheter.

2. An endotracheal suction catheter apparatus comprising:

a catheter configured for removing fluids from a respiratory tract of a patient by applying negative pressure to a lumen of said catheter;

a distal end configured to allow said catheter to be moved through said distal end and into the respiratory tract of a patient, said distal end having a cleaning chamber disposed therein;

a flap disposed proximate to said cleaning chamber wherein when a distal tip of said catheter is in said cleaning chamber and negative pressure is applied to said catheter said flap is urged towards said catheter and secretions on said catheter are removed in said cleaning chamber, said flap disposed distally to said cleaning chamber;

a connection member attached to said distal end and configured for engaging said distal end to a heat and moisture exchanger; and an opening member disposed on said distal end and configured for opening the heat and moisture exchanger when said opening member engages the heat and moisture exchanger.

3. The endotracheal suction catheter apparatus of claim 2, wherein said connection member is a pair of arms pivotally attached to said distal end, each of said arms having at least one projection for aiding engagement between said arms and the heat and moisture exchanger, said arms pivotable by a user to engage said distal end to the heat and moisture exchanger and pivotable by a user to disengage said distal end from the heat and moisture exchanger.

4. The endotracheal suction catheter apparatus of claim 3, wherein each of said arms has a curved finger tab for use in aiding a user in pivoting said arms to engage and disengage said distal end to the heat and moisture exchanger.

5. The endotracheal suction catheter apparatus of claim 2, further comprising a cap engageable with said opening member when said distal end is disengaged from the heat and moisture exchanger, said cap configured to cover at least a portion of said opening member.

6. The endotracheal suction catheter apparatus of claim 5, further comprising a tether for connecting said cap to said distal end.

7. The endotracheal suction catheter apparatus of claim 5, wherein said cap has a pull tab for aiding a user in removing said cap from said opening member when said cap is engaged with said opening member.

8. The endotracheal suction catheter apparatus of claim 2, wherein said flap has a flap projection on the proximal side of said flap, said projection configured for engaging said catheter as said catheter is advanced both into and out of the respiratory tract of a patient, said projection helping to prevent secretions on said catheter from contacting a planar surface of said flap when said catheter is withdrawn from the respiratory tract of a patient.

9. The endotracheal suction catheter apparatus of claim 8, further comprising a port in fluid communication with said cleaning chamber for introducing a cleaning solution into said cleaning chamber.

10. The endotracheal suction catheter apparatus of claim 9, wherein said planar surface of said flap has an aperture therethrough for inducing a turbulent fluid flow in said cleaning chamber when said distal tip of said catheter is in said cleaning chamber and negative pressure is applied to said catheter.

11. The endotracheal suction catheter apparatus of claim 2, further comprising a heat and moisture exchanger having a receiving ridge engaged with said connection member and on said distal end.

12. An endotracheal suction catheter apparatus comprising:

a catheter configured for removing fluids from a respiratory tract of a patient by applying negative pressure to a lumen of said catheter;

a distal end configured to allow said catheter to be moved through said distal end and into the respiratory tract of a patient, said distal end having a cleaning chamber disposed therein;

a flap disposed proximate to said cleaning chamber wherein when a distal tip of said catheter is in said cleaning chamber and negative pressure is applied to said catheter said flap is urged towards said catheter and secretions on said catheter are removed in said cleaning chamber;

a connection member attached to said distal end and configured for engaging said distal end to a heat and moisture exchanger;

an opening member disposed on said distal end and configured for opening the heat and moisture exchanger when said opening member engages the heat and moisture exchanger; and a shipping plug configured for extending into said distal end such that said shipping plug limits movement of said flap.

13. The endotracheal suction catheter apparatus of claim 12, wherein said shipping plug has a plurality of projections which are configured to engage a ridge in said distal end such that said shipping plug is secured onto said distal end.

14. The endotracheal suction catheter apparatus of claim 13, wherein said shipping plug has four projections.

15. The endotracheal suction catheter apparatus of claim 12, wherein said shipping plug has a flange located thereon, said flange limiting the extension of said shipping plug into said distal end, said flange sized so as to prevent accidental insertion of the entire shipping plug into the heat and moisture exchanger.

16. The endotracheal suction catheter apparatus of claim 12, wherein said shipping plug has an insertion and removal tab located on one end configured for a user to grasp in order to insert and remove said shipping plug from said distal end.

17. An endotracheal suction catheter apparatus, comprising:

a distal end configured for allowing a catheter to be moved through said distal end and into the respiratory tract of a patient, said distal end defining a cleaning chamber wherein the catheter may be cleaned;

a flap located in said distal end and located on one end of said cleaning chamber, said flap affecting fluid flow within said cleaning chamber during cleaning of the catheter, said flap disposed distally to said cleaning chamber; and a connection member attached to said distal end and configured for releasably engaging a heat and moisture exchanger such that the catheter may be advanced through said distal end into the heat and moisture exchanger.

18. The endotracheal suction catheter apparatus of claim 17, further comprising an opening member disposed on said distal end and configured for opening the heat and moisture exchanger when said opening member engages the heat and moisture exchanger.

19. The endotracheal suction catheter apparatus of claim 17, wherein said connection member includes at least one arm formed thereon and capable of engaging the heat and moisture exchanger.

20. The endotracheal suction catheter apparatus of claim 17, wherein said connection member comprises at least two arms formed thereon, wherein said arms are disposed oppositely from each other and each of the at least two arms are capable of engaging the heat and moisture exchanger.

21. The endotracheal suction catheter apparatus of claim 20, wherein each of the at least two arms include a surface member capable of engaging the heat and moisture exchanger.

22. The endotracheal suction catheter apparatus of claim 21, wherein the surface member is a pair of barbs.

23. The endotracheal suction catheter apparatus of claim 21, wherein the surface member is a flange on an end of each of said arms.

24. The endotracheal suction catheter apparatus of claim 20, wherein each of said arms has a curved finger tab for use in aiding a user in pivoting said arms to engage and disengage said connection member to and from the heat and moisture exchanger.

25. The endotracheal suction catheter apparatus of claim 17, further comprising a heat and moisture exchanger having a receiving ridge engaged with said connection member on said distal end.

\* \* \* \* \*

UNITED STATES PATENT AND TRADEMARK OFFICE
CERTIFICATE OF CORRECTION

PATENT NO. : 6,588,427 B1
DATED : July 8, 2003
INVENTOR(S) : Wayne D. Carlsen, Chet M. Crump and Edward B. Madsen It is certified that error appears in the above-identified patent and that said Letters Patent is hereby corrected as shown below:

<u>Title page, Item [54] and Column 1, line 2,</u>
Title, incorrect, please delete "TO" and substitute therefore -- FOR --.

<u>Title page,</u>
Item [56], FOREIGN PATENT DOCUMENTS, please delete "WO09903526 1/1999" and substitute therefore -- WO9903525 1/1999 --.

Signed and Sealed this

Twenty-third Day of December, 2003

JAMES E. ROGAN
*Director of the United States Patent and Trademark Office*